US 6,635,049 B1

(12) United States Patent
Robinson et al.

(10) Patent No.: US 6,635,049 B1
(45) Date of Patent: *Oct. 21, 2003

(54) DRUG BOLUS DELIVERY SYSTEM

(75) Inventors: Reginald D. Robinson, Plymouth, MN (US); Mark Lent, Brighton Park, MN (US); Chris C. Christiansen, Oakdale, MN (US)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,790

(22) Filed: Apr. 30, 1999

(51) Int. Cl.[7] .................... A61K 9/22; A61M 37/00; A61M 31/00
(52) U.S. Cl. ................. 604/891.1; 604/66; 604/132
(58) Field of Search .................. 604/93, 65, 66, 604/67, 891.1, 890.1, 242, 151, 241, 132, 133, 141, 142; 128/DIG. 12, DIG. 1, DIG. 13

(56) References Cited

U.S. PATENT DOCUMENTS

| | | | |
|---|---|---|---|
| 3,923,060 A | * 12/1975 | Ellinwood, Jr. | 128/DIG. 1 |
| 4,003,379 A | * 1/1977 | Ellinwood, Jr. | 128/DIG. 1 |
| 4,146,029 A | * 3/1979 | Ellinwood, Jr. | 128/903 |
| 4,193,397 A | 3/1980 | Tucker et al. | |
| 4,258,711 A | 3/1981 | Tucker et al. | |
| 4,350,155 A | * 9/1982 | Thompson | 604/891.1 |
| 4,443,218 A | * 4/1984 | DeCant, Jr. et al. | 604/67 |
| 4,619,653 A | * 10/1986 | Fischell | 128/DIG. 13 |
| 4,673,391 A | * 6/1987 | Kondo et al. | 604/141 |
| 4,714,462 A | * 12/1987 | DiDomenico | 604/67 |
| 4,718,893 A | 1/1988 | Dorman et al. | |
| 5,113,859 A | 5/1992 | Funke | |
| 5,158,547 A | 10/1992 | Doan et al. | |
| 5,281,210 A | * 1/1994 | Burke et al. | 604/141 |
| 5,328,460 A | * 7/1994 | Lord et al. | 604/67 |
| 5,382,236 A | * 1/1995 | Otto et al. | 604/141 |
| 5,387,419 A | 2/1995 | Levy et al. | |
| 5,443,450 A | * 8/1995 | Kratoska et al. | 604/141 |
| 5,507,737 A | * 4/1996 | Palmskog | 604/891.1 |
| 5,527,344 A | 6/1996 | Arzbaecher et al. | |
| 5,551,849 A | * 9/1996 | Christiansen | 604/141 |
| 5,575,770 A | * 11/1996 | Melsky et al. | 604/93 |
| 5,607,418 A | * 3/1997 | Arzbaecher | 604/891.1 |
| 5,667,504 A | * 9/1997 | Baumann et al. | 604/891.1 |
| 5,704,520 A | * 1/1998 | Gross | 604/141 |
| 5,716,318 A | 2/1998 | Manning | |
| 5,769,823 A | * 6/1998 | Otto | 604/141 |
| 5,810,015 A | * 9/1998 | Flaherty | 128/899 |
| 5,817,131 A | 10/1998 | Elsberry et al. | |
| 5,908,414 A | * 6/1999 | Otto et al. | 604/891.1 |
| 5,976,109 A | * 11/1999 | Heruth | 604/140 |

FOREIGN PATENT DOCUMENTS

| | | |
|---|---|---|
| EP | 0 362 611 B1 | 4/1990 |
| WO | WO 87/04629 A1 | 8/1987 |
| WO | WO 97/07840 A1 | 3/1997 |

* cited by examiner

*Primary Examiner*—Michael J. Hayes
(74) *Attorney, Agent, or Firm*—Banner & Witcoff, Ltd.

(57) ABSTRACT

An bolus delivery system includes an implantable pump, a sensor for sensing an adverse patient condition, such as atrial fibrillation, and a catheter for delivery of a bolus of drug to a target area of a living body. The pump is provided with a bolus metering assembly which includes, in a preferred embodiment, an auxiliary bellows defining a bolus reservoir in addition to the main reservoir of the pump. The auxiliary bellows is selectively placed in fluid communication with the pressurized main supply of drug via an inlet valve to refill the bolus reservoir. An outlet valve is provided to permit egress of the bolus to the catheter from the bolus reservoir. A drive train including a stepper motor and a face cam selectively opens and closes the inlet and outlet valves to effect accumulation or metering and delivery of the bolus. The auxiliary bellows is preferably provided as a collapsible element resiliently biased to an expanded position and is collapsed under pressure in the main reservoir to expel the bolus.

8 Claims, 5 Drawing Sheets

DRUG BOLUS DELIVERY SYSTEM

BACKGROUND OF THE INVENTION

1. Field of the Invention

The present invention relates to implantable devices for delivering beneficial agents or drugs to a living body. More particularly, the present invention relates to implantable devices for metering and delivering a drug bolus to a target area in a living body in response to sensed adverse patient conditions.

2. Description of the Related Art

Cardiac arrhythmias, which are irregularities in cardiac rhythms, adversely affect millions of individuals. Atrial fibrillation is likely the most common cardiac arrhythmia and may result in dizziness, weakness and other adverse effect. Moreover, atrial fibrillation, may result in death if it leads to ventricular fibrillation. Accordingly, significant efforts have been undertaken to provide therapy to prevent or relieve atrial fibrillation. Such efforts have included drug therapy, in the form of oral or intravenous drugs, and electrical defibrillation techniques.

Implantable systems are known for detecting the onset of fibrillation and providing a patient with electronic countermeasures. For example, U.S. Pat. No. 5,817,131, which is incorporated herein by reference in its entirety, discloses an implantable atrial defibrillators which includes implements for monitoring electrical activity of the heart and providing cardioversion countermeasures as well as pain relief therapy to the central nervous system in response to detection of the onset of atrial fibrillation or other adverse conditions.

There is a current trend towards the use of implantable drug delivery systems to provide site-specific and/or sustained delivery of beneficial agents to address adverse patient conditions, such as atrial fibrillation. Such delivery systems may include implantable infusion pumps, which typically include a pressurized drug reservoir and some form of fluid flow control. One example of an implantable infusion pump is the SYNCHROMED™ pump manufactured by Medtronic, Inc. of Minneapolis, Minn.

In atrial defibrillation applications, drug delivery systems must be capable of rapidly and accurately metering and delivering one or more drug boluses to a target area in response to the detection of an adverse condition, such as atrial fibrillation. Known drug infusion pumps, however, are not adapted to rapidly meter and deliver such drug boluses. There is thus a need for an implantable infusion pump which is capable of rapidly and accurately metering and delivering one or more boluses of drug in response to a detected adverse condition.

SUMMARY OF THE INVENTION

The present invention solves the aforementioned problems and others by providing an implantable pump which is capable of metering a drug bolus and delivering a drug bolus in response to a detected condition of atrial fibrillation. In a preferred embodiment, an implantable pump is provided with a control module which processes incoming signals from sensors to detect the onset of an adverse, patient condition. The pump is provided with a bolus metering assembly which is driven by a drive train in response to command signals from the control module. The bolus metering assembly includes an inlet valve which is adapted to permit ingress of pressurized drug-containing fluid from a pressurized main bellows reservoir into a collapsible auxiliary bellows that defines a bolus reservoir. An outlet valve is also provided to permit egress of the bolus of drug from the bolus reservoir after an appropriate amount of drug has accumulated therein. The inlet and outlet valves are driven by valve tappets, which are driven by a face cam, that provides the proper timing sequence for opening and closing the inlet and outlet valves. According to one aspect of the invention, the auxiliary bellows defining the bolus reservoir is exposed to the pressure in the main reservoir such that pressure in the main reservoir is used to expel the bolus of drug from the bolus reservoir.

In another embodiment, the bolus metering assembly is provided with a flow restrictor instead of an inlet valve. A cam drives the outlet valve to permit egress from the bolus reservoir after a predetermined amount of drug-containing fluid has flowed through the inlet restrictor. An auxiliary valve is provided within the auxiliary bellows reservoir and is adapted to engage an outlet port and abruptly stop the egress of the bolus when the auxiliary bellows is fully collapsed.

BRIEF DESCRIPTION OF THE DRAWINGS

The invention will be described with reference to the drawings, which form a part of this specification. Those of ordinary skill will understand that the invention is not intended to be limited to the exemplary embodiments illustrated in the drawings, of which.

DETAILED DESCRIPTION OF THE INVENTION

Figure 1:
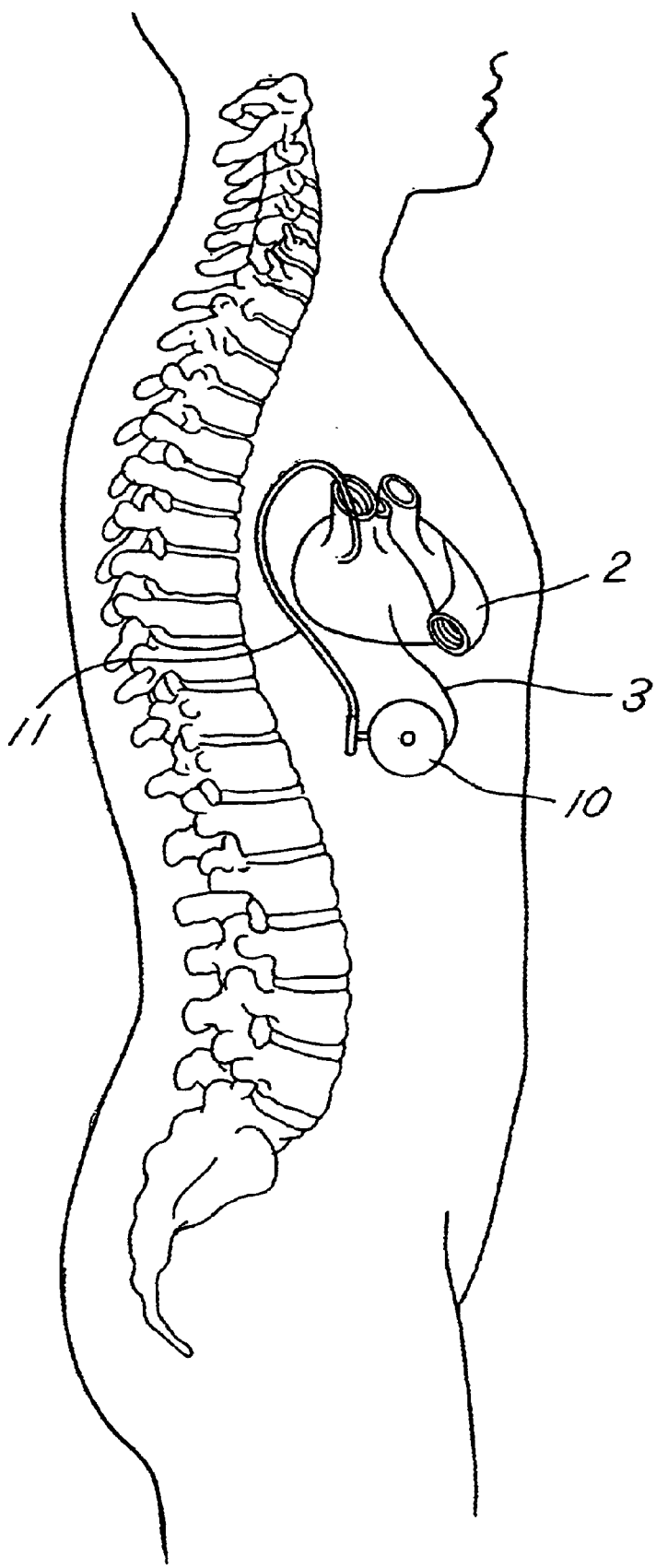
FIG. 1 is an illustration of an implanted drug delivery system incorporating a pump including a bolus delivery system according to a preferred embodiment of to the present invention.

Referring to FIG. 1, a bolus drug metering system according to the present invention comprises generally a bolus metering pump 10 which communicates with a drug delivery catheter 11 which is implanted in the tissue of a human heart 2 for delivering a beneficial agent or drug thereto. Also implanted in the tissue of the human heart is a sensing lead 3 which is adapted to sense electrical conditions at a specific location in the human heart to thereby detect the onset of atrial fibrillation. Sensing lead 3 communicates signals to pump 10 and processing circuitry which is described in U.S. Pat. No. 5,817,131, referenced above. Sensing lead 3 is preferably a contact type of lead for sensing atrial fibrillation.

Figure 2:
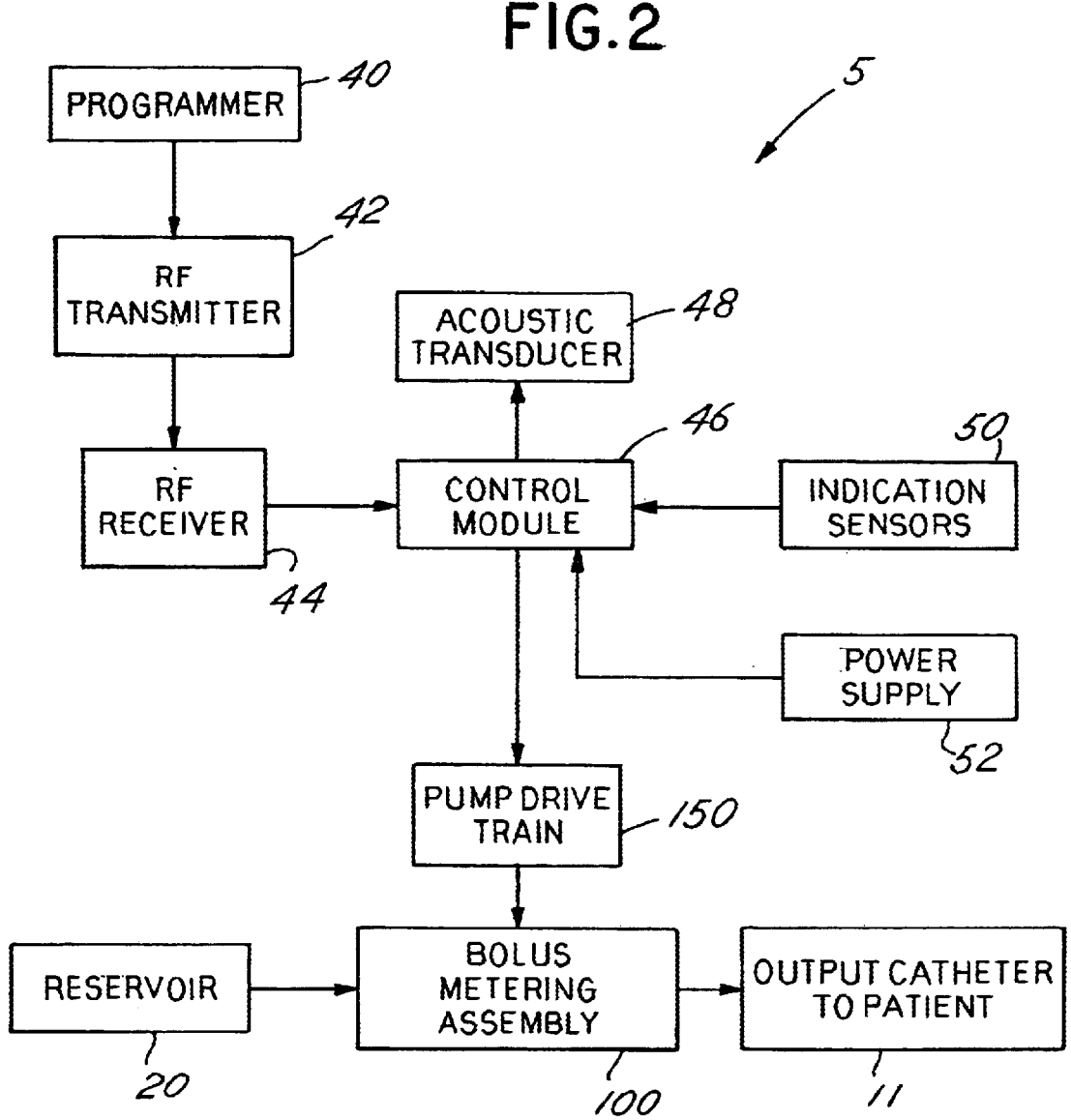
FIG. 2 is a block diagram of a bolus delivery system according to a preferred embodiment of the invention.

Referring now to FIG. 2, a bolus delivery system 5 according to a preferred embodiment of the present invention comprises generally a programmer 40 which provides signals to a radio frequency (RF) transmitter 42, which, in turn, provides radio signals to an RF receiver 44 onboard the implanted pump 10. As an example, programmer 40 may comprise a modified Medtronic Model No. 9790 programmer with atrial defibrillation software. RF receiver 44 provides signals to control module 46 which may be a microprocessor based computer onboard the pump 10 and which may be provided with instructions for processing data received from indication sensors 50. For example, the Medtronic Model 7250 atrial defibrillator hybrid which incorporates atrial fibrillation detection algorithms may be used for sensor signal processing and operation of the pump motor for drug delivery when fibrillation is detected.

Control module 46 provides signals to an acoustic transducer 48 which is used to produce an:audible signal to alert the patient that sensed conditions indicate the onset of atrial fibrillation. Indication sensors 50 may include the sensing lead 3 and other implanted sensing devices in the human body. An onboard power supply 52, for example a Medtronic PROMEON™ battery may be used to power the device.

Control module 46 provides signals to a pump drive train 150 which in turn drives the bolus metering assembly 100, the operation of which will be explained in detail below. Bolus metering assembly receives drug from a pressurized reservoir 20 and supplies drug in metered dosages to the output catheter 11 which delivers the drug to the body of the patient. Preferably, the pump drive train 150 comprises a motor and driving components similar to those used on the SYNCHROMED model pump manufactured by Medtronic, Inc.

Figure 3:
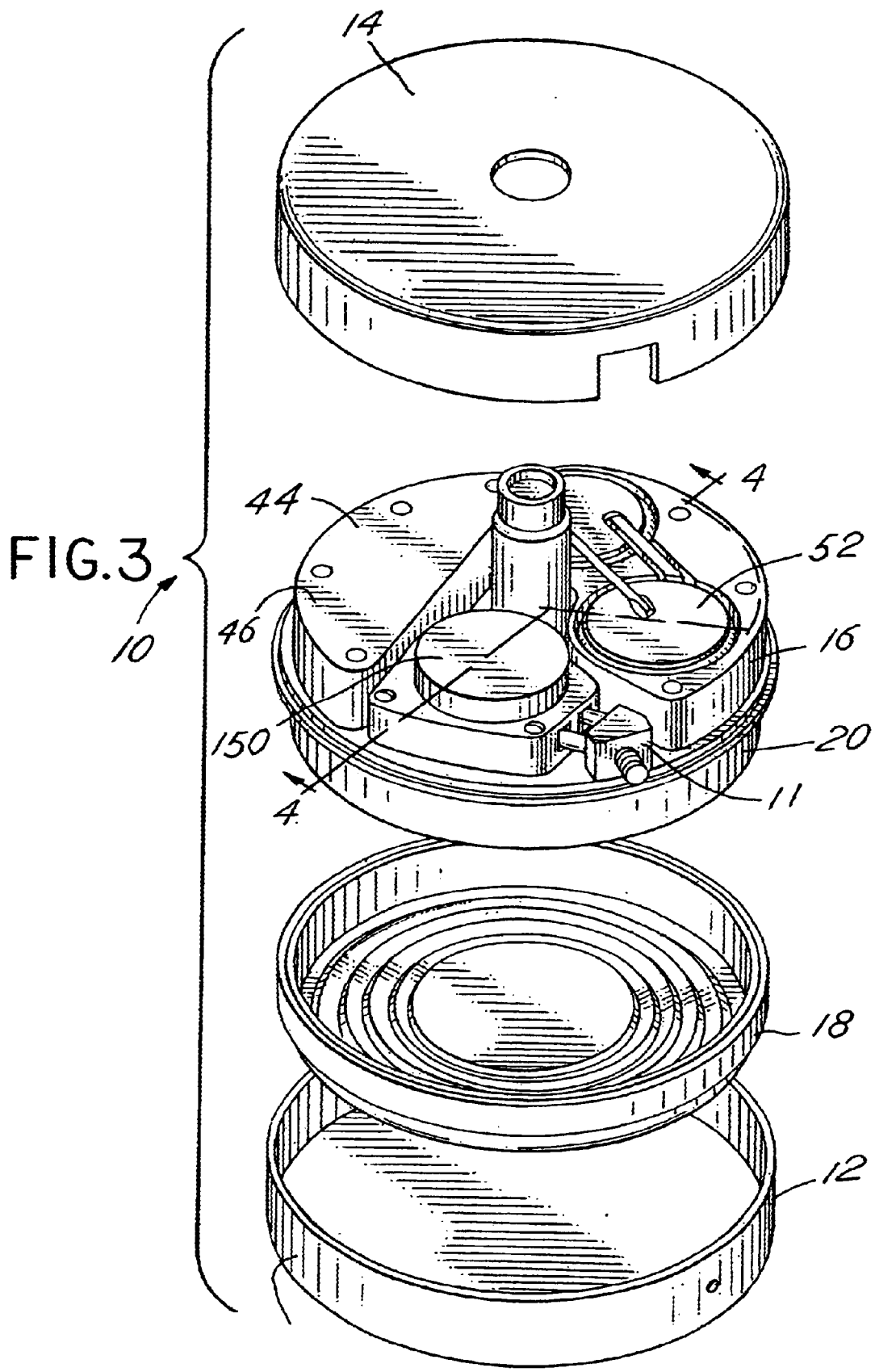
FIG. 3 is an exploded view of a pump according to a preferred embodiment of the present invention.
Figure 4:
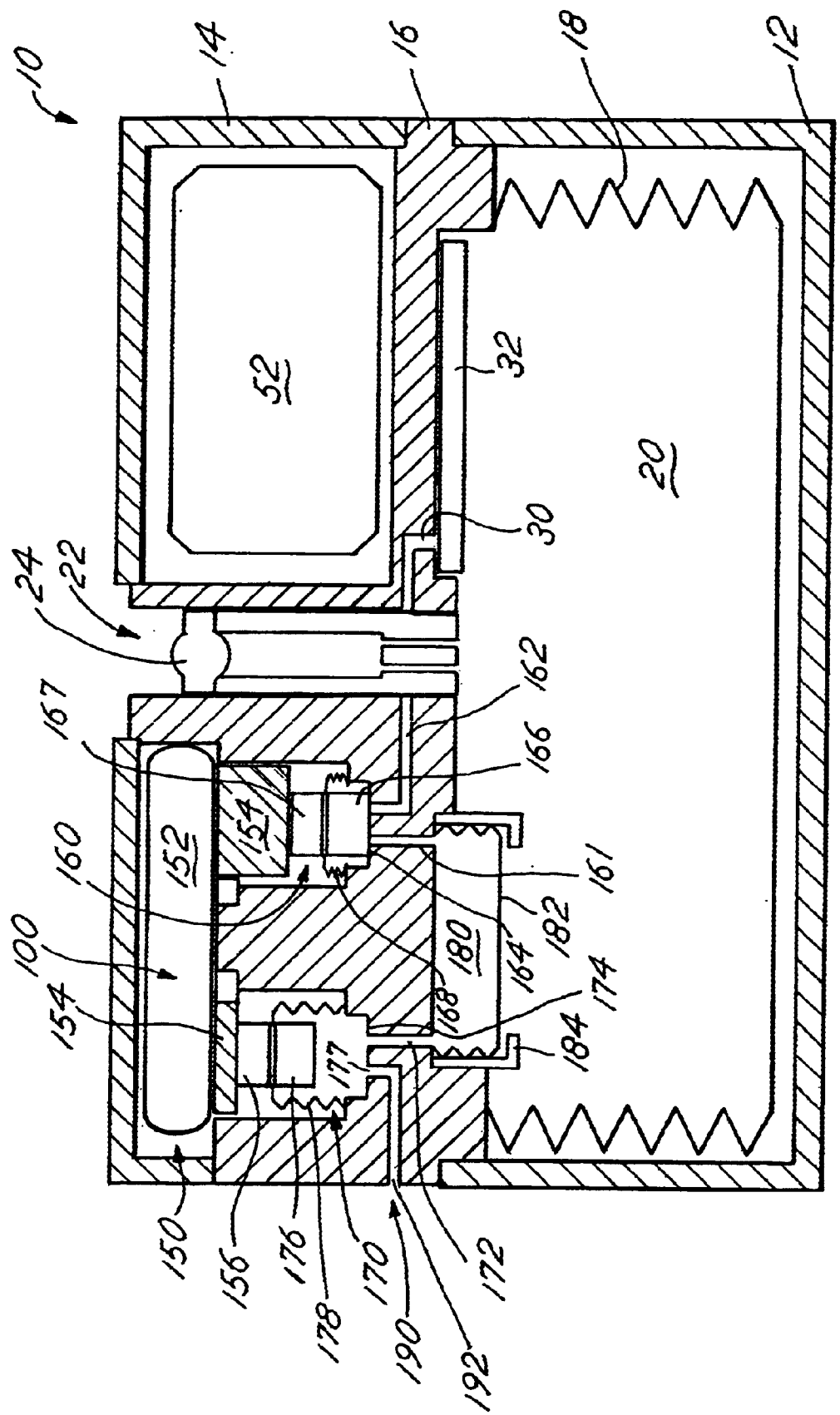
FIG. 4 is a cross-section taken along lines 4—4 of FIG. 3.

Referring now to FIGS. 3 and 4, the bolus metering pump 10 according to a preferred embodiment of the invention comprises generally a pump body which encloses a pressurized main reservoir 20 which is in fluid communication, via drug outlet passage 30, with a bolus metering assembly 100. Bolus metering assembly 100 generally comprises an inlet valve 160, an outlet valve 170, and a bolus storage chamber 180.

The implantable pump 10 includes a back shield 12, and a top shield 14 and a bulkhead 16. The back shield 12 and bulkhead 16 enclose the main reservoir 20. An open end of bellows 18 is fastened at to the bulkhead 16 in a known manner. As will be recognized by those of ordinary skill, bellows 18 is manufactured as an expandable and collapsible element. Main reservoir 20 is typically provided with a main supply of drug and pressurized by a propellant, typically a fluorocarbon, which occupies the space between the bellows 18 and the pump backshield 12 and which maintains a constant pressure or gas-spring on the bellows 18. A refill port 22 is provided for permitting refill of the main reservoir 20 with a desired drug and comprises a septum 24 for sealably receiving a hypodermic needle (not shown) for providing a refill supply of the desired drug to the reservoir 20.

Bulkhead 16 includes the main reservoir drugs outlet passage 30 in fluid communication with the interior of bellows 18 to convey drug from the main reservoir 20 to the bolus metering assembly 100. Preferably, a bacteriostatic filter 32 is provided upstream of outlet passage 30 to prevent the introduction of harmful bacteria into the bolus supply of drug. Main reservoir drug outlet passage 30 communicates with the inlet valve 160. It will be recognized that the drawing in FIG. 4 shows a portion of the main reservoir drug outlet passage 30 that is hidden in the drawings by the refill port 22.

Inlet valve 160 includes an inlet valve inlet port 162 and an inlet valve outlet port 167, both of which may be sealed by an inlet valve seal 166 when it rests in a sealing position (shown in FIG. 4) on an inlet valve seat 164. An inlet valve diaphragm 168 is provided to isolate the inlet valve seal 166 and the drug flowing therein from the pump drive train 150.

Diaphragm 168, which is pressurized on its interior, by the pressurized drug in a bolus storage chamber 180 provides an upward bias on the inlet valve seal 166. The inlet valve 160 is actuated via an inlet valve tappet 167 which is operated by a generally circular face cam 154, which is shown in cross-section in FIG. 4 as having typical cam raised and lowered portions.

Inlet valve outlet port 161 is in fluid communication with a bolus storage chamber 180 which is defined by the interior of a round auxiliary bellows 182. Auxiliary bellows 182 is provided as a deformable element which is biased towards its expanded position, for example, by construction of a material that elastically deforms, but does not yield, as bellows 182 travels from its expanded position to its collapsed position. A stop member 184 encircles the auxiliary bellows 182 and limits its expansion.

The interior of auxiliary bellows 182 and therefore the bolus storage chamber 180 are in fluid communication with an outlet valve 170. The outlet valve 170 includes an outlet valve inlet port 172 to permit the ingress of fluid from the bolus storage chamber 180. Outlet valve 170 also includes an outlet valve outlet port 177 which is in communication with pump outlet 190 and a catheter port 192 to permit the egress of fluid from the outlet valve 170 for delivery of a drug to a catheter (as seen in FIG. 1). Both outlet valve inlet port 172 and outlet valve outlet port 177 may be sealed by the outlet valve seal 176 when the cam face 154 is rotated to a selected position by the drive train 150. Like inlet valve 160, outlet valve 170 is also provided with a diaphragm 178 for sealing the outlet valve seal 176 and the outlet valve seat 174 and for providing an upward bias on the outlet valve seal 176.

The drive train 150 includes drive train stepper motor 152 which rotates the face cam 154 to cause reciprocal movement of the inlet valve tappet 167 and a similar outlet valve tappet 156. As will be recognized by those of ordinary skill, face cam 154 is provided with contoured surfaces to cause appropriate motion and timing of the opening and closing of the inlet valve 160 and outlet valve 170. The valve tappets 167 and 156 in turn actuate the inlet and outlet valve seals 166 and 176 to provide for the ingress of drug into the bolus storage chamber 180 and the subsequent egress of the bolus from the bolus storage chamber 180.

In operation, the bolus storage chamber 180 is first filled in the following manner. Face cam rotates to a position in which the inlet valve 160 is open and thereby the inlet valve seal 166 is removed from the valve seat 164 to permit the passage of drug from the main reservoir outlet passage 30 into the bolus storage chamber 180. Those of ordinary skill will recognize that drug will flow from the main reservoir 20 into the bolus storage chamber 180 as a result of the drug being under presure in the main reservoir 20 and as a result of the resilient bias on the auxiliary bellows 182 to expand to the expanded position shown in FIG. 4 where the outer periphery of auxiliary bellows 182 contacts the stop member 184. This action is much the same as the tendency of a medicine dropper bulb to return to its undeformed position after deformation. As the face cam 154 continues to rotate, inlet valve 160 will close to prevent further ingress of drug into the bolus storage chamber 180. Closure of the inlet valve 160 also isolates the pressure within the main bellows reservoir 20 from the interior of the auxiliary bellows 182. After closure of the inlet valve 160, continued rotation of face cam 154 results in opening of the outlet valve 170, thus permitting the egress of the accumulated drug within the bolus storage chamber 180 into the catheter port 192. It will be recognized that the opening of outlet valve 170 will permit the escape of drug from bolus storage chamber 180, the impetus for which is provided by the exposure of the bolus storage chamber 180 to a lower pressure namely that in the catheter". Thus, the auxiliary bellows 182 will collapse under the pressure from the drug in the main reservoir 20 with the resulting expulsion of drug into the catheter port 192 through the catheter", and ultimately to the heart 2. Further continued rotation of the face cam 154 results in closure of the outlet valve 170 and later, reopening of the inlet valve 160 to permit the ingress of another dose of drug into the auxiliary bellows 182. Delivery of drug may then be repeated for another episode of atrial fibrillation if needed.

It will be recognized by those of ordinary skill that other mechanical implements besides those described above may be used to control the inlet and outlet valves. For example, face cam 154 and tappets 167 and 176 may be replaced by radial acting cams, groove acting cams, roller cams, or other linkage systems. In addition, it will also be recognized by those of ordinary skill that the reservoirs and dosing chambers construction may be comprised of metal, plastic or ceramic materials.

Figure 5:
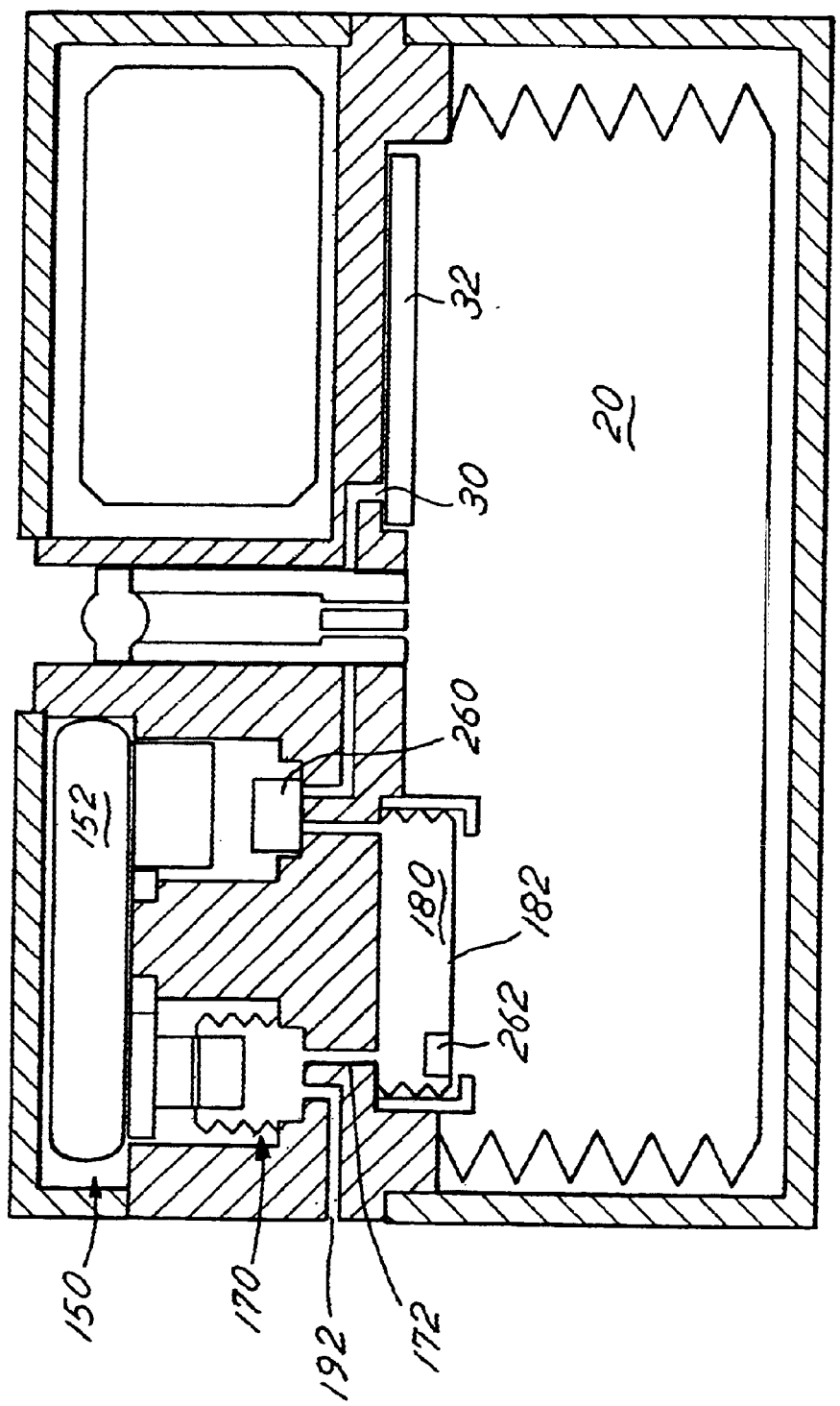
FIG. 5 is a cross-section of a pump including a bolus delivery system according to another preferred embodiment of the present invention.

FIG. 5 illustrates a cross section of another preferred embodiment of the present invention. In this embodiment, the inlet valve 160 of the aforementioned embodiment is replaced with a flow restrictor 260 and a valve seal 262 provided on an interior surface of the auxiliary bellows 182 and positioned to engage outlet valve inlet port 172 when auxiliary bellows 182 is in its collapsed position. According to this embodiment, refill of the bolus storage chamber 180 proceeds in the following manner. The auxiliary bellows 182, after collapsing, will cause the valve 262 to seal off the outlet valve inlet port 172 and prevent further egress of drug from the interior of auxiliary bellows 182. Drug continues to flow from the main reservoir 20 through the main reservoir outlet passage 30, through the flow restrictor 260 and into the bolus storage chamber 180 at a predetermined rate. Thus, the auxiliary bellows 182 will be refilled with a supply of drug. When fibrillation is detected, the control module will activate the motor 152 of the drive train 150 thereby causing the outlet valve 170 to open and permit the flow of the bolus into the outlet catheter port 192. During delivery of the bolus, the restrictor 260 functions as a virtually closed valve due to its low flow rate and the relatively high flow rates out through the outlet valve 170 and catheter port 192. The seal 262 on the interior of auxiliary bellows 182 functions to abruptly stop flow of drug from the bolus reservoir 180 and to thereby provide precise control of the metered amount of drug.

Although the preferred embodiment of this invention has been described above in some detail, it should be appreciated that a variety of embodiments will be readily apparent from the foregoing description to persons of ordinary skill. For example, it will be recognized that more than one bolus metering assembly may be provided on a single pump, to permit rapid successive delivery of more than one drug bolus, when needed. The description is intended to be illustrative of the preferred embodiment of this invention and not intended to be limiting to the scope of protection sought by the applicants, which scope is defined by the appended claims.

What is claimed is:

1. A pumping mechanism, entirely implantable in a living body, for delivering a bolus of a beneficial drug agent to a preselected location in said living body, said living body having a known body pressure, said mechanism comprising:

(a) a channel in said living body interconnecting said pumping mechanism with said preselected location in said living body, said channel providing a flow path for said bolus of said drug agent;

(b) a sensor in said living body for sensing an adverse condition in said living body and transmitting a signal of said adverse condition;

(c) a normally enclosed first reservoir onboard said pumping mechanism for storing a bolus amount of said beneficial drug agent at a preselected first pressure level which is greater than said body pressure, said first reservoir comprising a flexible deformable bellows member being movable between an expanded position and a collapsed position, said bellows member having an interior portion for storing said bolus drug and also having an exterior portion defining said interior portion, said bellows member being at said expanded position when storing said bolus amount of said drug agent at said first pressure level;

(d) a second reservoir onboard said pumping mechanism and containing a supply of said drug agent in an amount greater than said bolus amount, said supply of said drug agent in said second reservoir normally being in pressurized communication with said exterior portion of said bellows member at said first pressure level;

(e) a valve onboard said pumping mechanism and interconnected in said flow path and being positioned between said first reservoir and said channel, said valve having a first valve position and a second valve position and being moveable between said first valve position and said second valve position, said drug agent being maintained at said first pressure level in said interior storage chamber when said valve is in said first position;

(f) a power supply onboard said pumping mechanism; and (g) a metering and drive assembly, onboard said pumping mechanism, said metering and drive assembly being operatively connected to said sensor and being capable of receiving said signal of said adverse condition, said metering and drive assembly also being operatively connected to said power supply for driving said valve from said first valve position to said second valve position upon receiving said signal, said channel thereby openly communicating with said first reservoir as said valve is being moved to said second valve position, the drug agent in said second reservoir acting against said bellows of said first reservoir for driving said bellows to the collapsed position and thereby driving said bolus drug agent in said first reservoir through said flow path from said first reservoir past said valve, said bolus drug amount thereby being delivered to said living body, said passage of said drug agent being in response to said greater pressure in said first reservoir relative to said body pressure.

2. The pumping mechanism of claim 1 including a control module operatively associated with said sensor and with said power supply, the control module causing said power supply to activate said metering and drive assembly in response to said signal of said adverse patient condition.

3. The pumping mechanism of claim 1 wherein said second reservoir comprises a bellows surrounding said first reservoir and which is normally biased toward an expanded position.

4. The pumping mechanism of claim 3, which further includes stop members for limiting the expansion of both said bellows of both said first and second reservoirs.

5. The pumping mechanism of claim 1 which includes a flow passage for conveying a bolus amount of said drug agent from said supply of said drug agent in said second reservoir to said first reservoir after said bolus amount of said drug agent is delivered from said first reservoir to said second reservoir.

6. The pumping mechanism of claim 5 wherein said bellows of said first reservoir is self biased to said expanded position as said bolus of said drug agent is being delivered from said second reservoir to said first reservoir thereby refilling a bolus amount of said drug agent in said first reservoir.

7. The pumping mechanism of claim 5 wherein said valve comprises a flow restrictor for permitting a predetermined rate of ingress of said drug agent from said second reservoir to said first reservoir.

8. The pumping mechanism of claim 1 wherein said metering and driving assembly includes a cam mechanism for selectively and rotatably operating said valve between said first valve position and said second valve position.

* * * * *